United States Patent [19]

Riegger et al.

[11] Patent Number: 4,484,483
[45] Date of Patent: Nov. 27, 1984

[54] NEEDLE ASSEMBLY USEFUL IN THE HEAD-SPACE METHOD OF GAS CHROMATOGRAPHY

[75] Inventors: Wolfgang Riegger, Salem-Beuren; Wolfgang Chlosta, Überlingen, both of Fed. Rep. of Germany

[73] Assignee: Bodenseewerk Perkin-Elmer & Co., GmbH, Überlingen, Fed. Rep. of Germany

[21] Appl. No.: 354,409

[22] Filed: Mar. 3, 1982

[30] Foreign Application Priority Data

Mar. 13, 1981 [DE] Fed. Rep. of Germany ....... 3109616

[51] Int. Cl.³ .......................................... G01N 35/00
[52] U.S. Cl. ................................................. 73/864.23
[58] Field of Search .......... 73/863.85, 864.01, 864.21, 73/864.23, 864.24, 864.25, 864.74, 864.84, 864.85, 864.86, 864.87

[56] References Cited

U.S. PATENT DOCUMENTS 3,545,279 12/1970 Jentzsch .
3,754,443  8/1973 Harris, Sr. et al. .............. 73/864.21
4,117,727 10/1978 Friswell et al. ................. 73/864.21
4,199,988  4/1980 Riegger .

Primary Examiner—S. Clement Swisher
Attorney, Agent, or Firm—E. T. Grimes

[57] ABSTRACT

A needle assembly for feeding a carrier gas into a sample vessel during the head-space analysis of a sample includes a lateral outlet passage for conveying the gas.

7 Claims, 2 Drawing Figures

NEEDLE ASSEMBLY USEFUL IN THE HEAD-SPACE METHOD OF GAS CHROMATOGRAPHY

BACKGROUND OF THE INVENTION

The present invention generally relates to a needle assembly for feeding a carrier gas into a sample vessel sealed by a self-sealing diaphragm and, in particular, relates to an assembly useful wherein a housing is movable relative to the instrument-fixed needle, which needle includes a lateral exit aperture at its lower end.

A state of equilibrium is obtained in the head space above a sample liquid in a sample vessel sealed by a diaphragm, in which state of equilibrium the partial pressures of the sample components in the head space unambiguously depend on the composition of the sample. In a sampler operating on the head-space method, the sample applied to the separating column of a gas chromatograph is taken from this head space. To this end, a needle is pierced through the self-sealing diaphragm. The needle is connected to the inlet of an injection block of the gas chromatograph. Furthermore, an injection block is connected to a carrier gas conduit. A shut-off valve is disposed in this carrier gas conduit. With the shut-off valve opened, carrier gas flows, at first, into the head space of the sealed sample vessel through the needle such that the carrier gas pressure builds up within the sample vessel. This does not affect the partial pressures of the sample components in the head space. When the shut-off valve is closed subsequently, the carrier gas pressure in the injection block will break down. Then a gas sample is pressed from the head space into the injection block due to the elevated pressure in the sample vessel. After a preselected defined time interval, the shut-off valve is opened again, whereby the dosing is terminated, and the gas sample having reached the injection block is transported through the separating column of the gas chromatograph by the carrier gas flow.

To prevent a further unrestricted flow of carrier gas out of the needle, when the needle is removed from the sample vessel, it is known (German Pat. No. 1 284 660) to dispose the needle in a piston sealingly movable within a cylinder. The cylinder includes a restricting outlet and is sealed by another self-sealing diaphragm at its end face facing the sample vessel. The piston is loaded by a compression spring trying to move the piston away from this self-sealing diaphragm and to retract the needle into the interior of the cylinder.

In one conventional device, the needle is stationary and is permanently connected to the injection block and to the carrier gas conduit. The cylinder is guided for longitudinal movement relative to this fixed needle. A sample vessel is caused to engage with its self-sealing diaphragm the end face of the cylinder sealed by the other self-sealing diaphragm and is pushed upwards, whereby the cylinder is urged back and the needle penetrates into the sample vessel through the two self-sealing diaphragms. A flushing flow flows through the needle in its position of rest, the intensity of this flushing flow being determined by the restriction of the outlet of the cylinder. This flushing flow ensures that there is no cross-contamination of vapors within the needle from one sample to the next one.

The self-sealing diaphragm is pierced with each sample dosing. After a certain number of piercings, the self-sealing diaphragm is so effectively destroyed that it has to be replaced. The necessity of replacing the self-sealing diaphragm is annoying and, additionally, impedes automation of the dosing of the samples.

Further, the deterioration of the self-sealing diaphragm is accelerated by the edges of the lateral exit aperture formed by a transverse bore.

Yet further, the needle of such a conventional device is mounted in a piston which forms a cylinder chamber together with the cylinder sealed by the self-sealing diaphragm. The cylinder chamber is connected to atmosphere only by means of the restricted outlet. The gas cushion formed therein would counteract the pushing-up of the cylinder. Therefore, another outlet governed by a solenoid valve is provided in practice, which other outlet is opened when the cylinder is pushed up.

From German Offenlegungsschrift No. 28 15 023 a needle assembly is known, in which the needle is guided for longitudinal movement within a stationary housing. The needle has a lateral entrance aperture in its portion remote from the tip, which entrance aperture is moved through a graphite seal and connected either to the unrestricted carrier gas conduit or to a chamber, to which a restricted carrier gas flow is supplied as a flushing flow. Thus, in this prior art needle assembly, the change-over to "flushing flow" is not caused on the exit side but on the entrance side of the needle. The prior art needle assembly requires a movable needle, which is unsuitable in many cases. Furthermore, restricted and separate therefrom, unrestricted carrier gas conduits are required thereby complicating the structure.

SUMMARY OF THE INVENTION

It is one object of the present invention to provide a needle assembly such that both the self-sealing diaphragm at the housing and the solenoid valve to be opened, when the housing is pulled up, may be omitted.

This object is achieved, at least in part, by a needle assembly having a housing bore, and a lateral outlet passage branching off the housing bore, which outlet passage is connected to the lateral exit aperture of the needle.

In its position of rest, the needle is located in the housing bore and is connected to the outlet passage and, through the restrictor, to atmosphere. When the housing is pushed up by an engaging sample vessel sealed by a self-sealing diaphragm, the needle is pierced through this diaphragm, and the lateral exit aperture exits the housing bore and is opened within the sample vessel, after the diaphragm has been pushed thereover.

Other objects and advantages will become apparent from the following detailed specification and the appended drawing.

BRIEF DESCRIPTION OF THE DRAWING

The invention is hereinafter described in greater detail with reference to the accompanying drawing, not drawn to scale, in which.

DETAILED DESCRIPTION OF THE INVENTION

Figure 1:
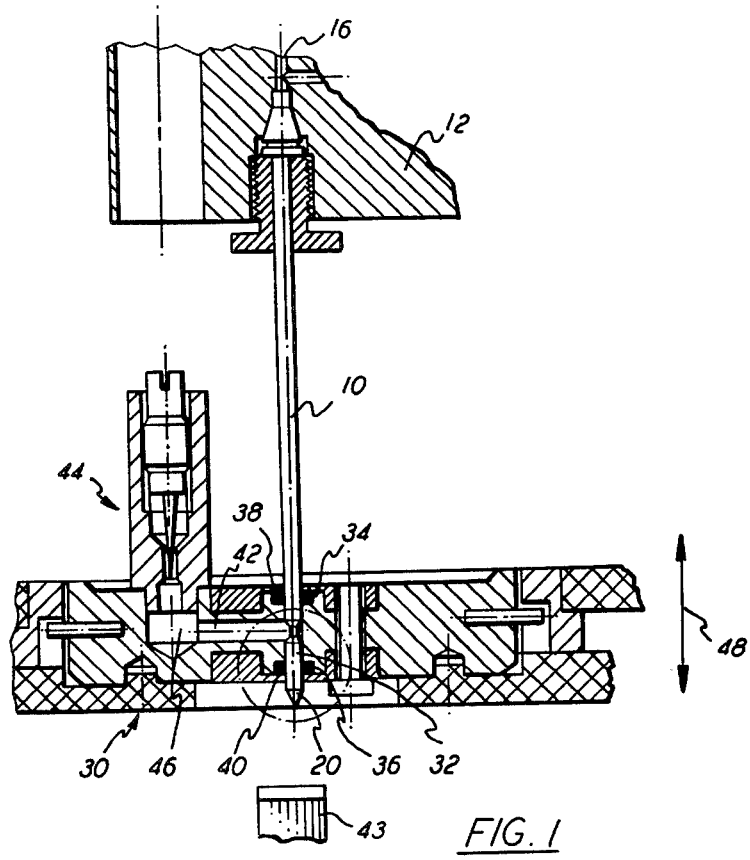
FIG. 1 is a sectional view of a needle assembly embodying the principles of the present invention.
Figure 2:
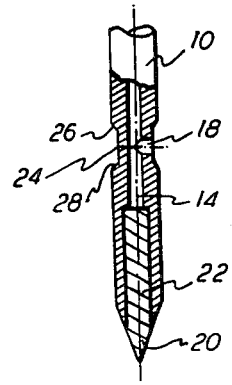
FIG. 2 is an exploded detail view of a portion of FIG. 1.

Referring to FIG. 1, a needle, generally indicated at 10, is fixedly mounted in the injection block 12 of a gas chromatograph. The needle 10 includes a longitudinal passage 14 therethrough connected to a carrier gas passage 16 within the injection block 12. The longitudinal passage 14 intersects with a transverse bore of the needle 10. This transverse bore forms a lateral exit aperture 18. A tip 20 is located at the end of the needle. The tip 20 is provided on an end piece 22 pressed into an enlargement of the longitudinal bore 14 and closing the longitudinal bore 14 on its end face. Thus, carrier gas flows from the carrier gas passage 16 through the longitudinal bore 14 and emerges laterally through the exit aperture 18.

Needle 10 preferably has an outer diameter of about 1.5 mm, whereas conventional needles have an outer diameter of about 1 mm. Further, needle 10 includes a circumferential groove 24 near the exit aperture 18. The lateral exit aperture 18 is preferably located at, or near, the bottom of the circumferential groove 24. The lateral walls 26 and 28 of the circumferential groove 24 are tapered such that the circumferential groove 24 becomes wider towards the outside. The edges of the circumferential groove 24 are preferably rounded and polished.

A housing 30 having a housing bore 32 which is surrounded by two spaced apart annular grooves 34 and 36 into which sealing rings, 38 and 40, respectively, preferably in the form of O-rings, are retained. A lateral outlet passage 42 branches off housing bore 32 between the sealing rings, 38 and 40. Outlet passage 42 is connected to atmosphere through a restrictor 44. To this end, outlet passage 42 terminates in a blind bore 46 parallel to housing bore 32. The adjustable restrictor 44 in the form of a needle valve is disposed in the blind bore 46.

The needle 10 extends through housing bore 32. The sealing rings, 38 and 40, sealingly engage the outer surface of the needle 10 and cause sealing between needle 10 and housing bore 32. Housing 30 is guided, by means well known in the art, for movement parallel to the needle 10, as indicated by double arrow 48. During the position of rest shown in FIG. 1, outlet aperture 18 is positioned between the sealing rings 38 and 40 and communicates with the outlet passage 42 via the circumferential groove 24.

When a sample vessel 43 of the type sealed by a self-sealing diaphragm is pressed against housing 30, the housing 30 moves upwards relative to the fixed needle 10. Thus, the needle 10 pierces the diaphragm of the sample vessel 43 with its tip 20. Sealing ring 40 passes the exit aperture 18 of needle 10. Thus, the exit aperture penetrates through the diaphragm and into the sample vessel 43. The carrier gas passage 16 is now connected to the head space of the sample vessel in substantially unrestricted manner via longitudinal passage 14 and exit aperture 18.

The needle assembly described above is particularly adapted for the automation of the sample feeding. Advantageously, no self-sealing diaphragm is required in the needle assembly, which diaphragm would be stressed in continuous operation and would form a wear part. Self-sealing diaphragms are only provided on the sample vessels. There, however, it is always another diaphragm being pierced with each sample dosing.

Damage or wear of sealing ring 40 by exit aperture 18 is substantially completely avoided due to the arrangement of lateral exit aperture 18 on the bottom of a circumferential groove 24. That is, the edges are rounded and polished.

With the housing bore 32 being moved, as described, along the needle 10, no trapped gas volume is compressed. Consequently, the outlet passage 42 need not be vented by any additional solenoid valve. This results in a simple and compact arrangement using a relatively short needle. Hence, the needle need not be heated by a separate heater, as in prior art instruments, but is heated by the injection block 12 via thermal conduction. Thereby, the structure is simplified and replacing of the needle is facilitated.

Although a detailed description is presented herein, other embodiments and arrangements are derivable therefrom. Thus, this description is descriptive and not limiting and defined by the appended claims and the reasonable interpretation thereof.

What is claimed is:

1. A needle assembly for feeding a carrier gas into the head space of a sample vessel sealed by a diaphragm, said assembly comprising:
   a hollow needle affixed to an analytical instrument, said needle having a lateral exit aperture at the lower end thereof;
   a housing movable with respect to said needle, said housing including a bore therethrough for guiding said needle, said bore branching into a lateral outlet passage, said passage communicating with said lateral exit aperture in said needle, when said housing is in a first position, said passage opening to the atmosphere through a restrictor, whereby when said housing is in a second position said communication between said bore and said passage is prevented.

2. Needle assembly as claimed in claim 1, further comprising:
   at least two spaced apart sealing rings positioned along said needle, said sealing rings forming a seal between said needle and housing bore, said rings being spaced such that said outlet passage is located therebetween.

3. Needle assembly as claimed in claim 2 wherein: said sealing rings are formed by O-rings.

4. Needle assembly as claimed in claim 1 wherein said restrictor includes an adjustable needle valve.

5. Needle assembly as claimed in claim 1 wherein: said needle includes a circumferential groove; and said lateral exit aperture is provided at the bottom of said circumferential groove.

6. Needle assembly as claimed in claim 5, wherein: the lateral walls of said circumferential groove are tapered such that said circumferential groove becomes wider towards the outside.

7. Needle assembly as claimed in claim 6 wherein: the edges of said circumferential groove are rounded and polished.

* * * * *